US00PP09798P

United States Patent [19]

Saville

[11] Patent Number: Plant 9,798

[45] Date of Patent: Feb. 11, 1997

[54] MINIATURE ROSE PLANT NAMED 'SAVAMOR'

[75] Inventor: F. Harmon Saville, Newburyport, Mass.

[73] Assignee: Nor'East Miniature Roses, Inc., Rowley, Mass.

[21] Appl. No.: 574,388

[22] Filed: Dec. 18, 1995

[51] Int. Cl.[6] ..... A01H 5/00

[52] U.S. Cl. ..... Plt./7.1

[58] Field of Search ..... Plt./7.1, 1, 9, 22, Plt./26–27

[56] References Cited

U.S. PATENT DOCUMENTS

P.P. 5,141 11/1983 Saville ..... Plt./8
P.P. 6,861 6/1989 Christensen ..... Plt./11

OTHER PUBLICATIONS

Haring, ed., 1986, "Modern Roses 9", The American Rose Society, Shreveport, Louisiana, pp. 47, 301.

*Primary Examiner*—Howard J. Locker

[57] ABSTRACT

'Savamor' is a miniature rose which can be grown quite satisfactorily in a greenhouse or as a hardy, garden perennial. It blooms continually throughout the growing season with bus and flowers in varying shades of mauve. The rose is most noted for its very strong and pleasant fragrance, similar to that fond in the lilac. Buds are urn-shaped as they start to open unfurling to exhibition form, and are most often borne singly on stems to to 12 inches long but also in sprays, making this plant ideal as both a specimen plant and for cut flowers. The plant grows to about 30 inches or more in height and has medium green, semi-glossy foliage. This variety does need winter protection in severe climates.

1 Drawing Sheet

BACKGROND OF THE INVENTION

The present invention relates to a new and distinct variety of hardy, bush type plant of the miniature rose class, which bears some resemblance to 'BENalav' (U.S. Pat. No. P.P. 6,517) which is its seed parent, in that both are tall miniature rose plants with light mauve flowers and strong fragrance.

This new and distinct rose plant of the miniature rose class can be grown quite satisfactorily in the greenhouse, as a garden perennial, as a specimen plant, or for cut flowers, needing protection through the winter in severe climates.

This new and distinct rose plant of the miniature rose class was created by crossing the following two rose plants: 'BENalav' (U.S. Pat. No. P.P. 6,517) as the seed parent, and 'AROgrewod' (U.S. Pat. No. P.P. 6,861) as the pollen parent. The cultivar name for this new rose is 'SAVamor'.

This new variety is distinguished by its:

A. Very strong lilac-like fragrance;
B. Buds and flowers in varing shades of mauve but with more of a pink tone than either its seed parent or its pollen parent;
C. Flowers that compare in size but with fewer petals than it's seed parent, and flowers that are much smaller in size than its pollen parent; and
D. Upright and somewhat open growth habit which is typical of both parent plants.

Asexual reproduction by cuttings of this new variety as performed in Essex County, Mass. and in San Bernardino County, Calif. has shown conclusively that all distinguishing characteristics of this new rose plant come true to form and are firmly fixed.

SUMMARY OF THE INVENTION

This new and distinct variety of miniature rose plant has flowers in varying shades of mauve, borne singly on stems up to 12 inches long and in sprays of up to seven. The plant itself grows 24 to 30+ inches tall at maturity and spreads out as wide as it is tall, in an upright, well branched but rather open habit with its most outstanding characteristic being its very strong lilac-like fragrance.

BRIEF DESCRIPTION OF THE DRAWING

The accompanying color photograph shows typical specimens of the vegetative growth and flowers of this new variety in different stages of development as seen and grown outside in early September in Essex County, Mass. Plant parts are depicted in color as true as reasonably possible in a color illustration of this character.

BOTANICAL DESCRIPTION OF THE PLANT

Following is a detailed description in outline form of the new and distinct cultivar of miniature rose plant. All major color plate identifications made are referring to The Royal Horticultural Society (R.H.S.) Colour Chart except where common terms of color definition are employed.

Type: Miniaure rose (*Rosa chinenis* 'minima'); hardy; outdoors; decorative; specimen plant; cut flowers; potted plant; greenhouse plant.
Seed parent: 'BENalav' (U.S. Pat. No. P.P. 6,517).
Polen parent: 'AROgrewod' (U.S. Pat. No. P.P. 6,861).
Flowers: Borne often singly on stems of up to 12 inches in length, but also in sprays of up to seven buds and opening flowers.
Quantity of bloom: Profuse.
Bud:
*Size and form.*—Averaging ¾ of an inch in length; ovoid; becoming urn shapre as sepals divide and petals start to unfurl.
*Sepals.*—Very finely toothed and occasionally one sepal with be sparsely foliated; lanceolate in shape; extending beyond the tip of the bud; coloration is R.H.S. 147B with outer side flushed with R.H.S. 1838B in the sun; as flower opens,the sepals rollout and back to the stem and cross over beyond the stem. As hip matures, sepals roll upward until they are straight up, perpendicular to the top of the hip, remaining attached until the hip drops from the plant.

*Color when sepals first divide.*—Between R.H.S. 59D and 60D; near 69C where petals are shielded from light by the sepals.

*Color when petals begin to unfurf.*—Near R.H.S. 65C flushed with a thin layer of 60D.

*Peduncle.*—Varying in length from one inch to one and ⅝ inches; erect and straight; color near R.H.S. 146D, flushed with 183B in the sun.

Bloom:

*Size when fully expanded.*—Average 2 inches to 2½ inches.

*Form.*—High-centered at first; becoming flat with the petals reflexing loosely outward and staying thus until dropping from the receptacle; bloom opens to show the center of the flower clearly.

*Petalage under normal conditions.*—24–30 petals arranged shingle-like, and 1–6 petaloids in the center of the flower.

*Fragrance.*—Very strong lilac-like fragrance.

Petals:

*Texture.*—Thick; inside velvety, outside satiny.

*Form.*—Broad fan shaped.

*Notable characteristics.*—Occasionally one petal or petaloid per flower will have a white streak going up through the center.

Color: (from plants grown outside in Essex County, Mass., in September 1995):

*When half open (outer petals).*—Inside surface — near R.H.S. 65D; outer edges flushed lightly near 59D, growing in intensity to the very edge of the petal. Outside surface — near 11D, flushed lightly with 59C.

*When half open (inner petals).*—Inside surface — near R.H.S. 62C. Outside surface — near 11D with edges of near 62D.

*Base of petals at attachment.*—R.H.S.11A.

*Color change as bloom ages.*—Not much of a color change; the R.H.S. 59D and 62D are the most intense as the flower first opens; fading to 65D, then staying at 65D, but flushed with 62D in all stages.

*General tonality.*—Newly opened flower — shades of medium and light mauve. Three days open — lightens to lighter shades of mauve.

Lasting quality:

*On plant.*—6–8 days depending upon conditions.

*As a cut flower.*—4–7 days or longer, depending on temperature.

Reproductive organs:

*Stamens.*—Abundant — 75 to 100, arranged regularly around styles.

*Filaments.*—Uneven in length, from 3/16 to ⅜ inches in length; coloration near R.H.S. 11D, and 11B toward base.

*Anthers.*—Near R.H.S. 11C in color.

*Pollen.*—Moderate quantity; near R.H.S. 22A in color.

*Pistils.*—About the same amount as stamens.

*Styles.*—Very thin; shorter than filaments, undulate and uneven in length; near R.H.S. 150D in color.

*Stigmas.*—Color near R.H.S. 150D.

*Hips.*—Globular in shape; up to 13/16 of an inch; color near R.H.S. 28B to near 30B; all seeds fully enclosed in ovary.

*Seeds.*—Medium in size and only a few per hip.

The plant:

*Habit.*—Upright, well branched yet open, spread roughly the same as the height.

*Growth.*—Vigorous, growing to 24 to 30 inches or more in height at maturity.

*Foliage.*—Small, compound of 5 (sometimes also 3 or 7) leaflets. Color of new foliage is (upper surface) near R.H.S. 147A, usually lightly flushed with 183A; and (under surface) near 147C, usually lightly flushed with 183A. Mature foliage coloration is (upper surface) near R.H.S. 147A; and (under surface) near 147B.

*Leaflet.*—Shape is ovate with acute tip; Upper surface is semi-glossy while underside is matte. Leaflet margin is finely and unevenly serrated.

*Rachis.*—Color is (upper surface) near R.H.S. 146C flushed with 183A, and (under surface) near 146D; one or two thorns on under side of stem of older leaves and a few prickles on under side of stem of younger leaves.

*Stipules.*—Very finely serrated, one slightly longer than the other, averaging ⅝ of an inch in length, attached to the leaf stem for ⅔ of their length, then turning slightly outward.

*New wood.*—Smooth with a color near R.H.S. 144B.

*Old wood.*—Near R.H.S. 137D in color, with the oldest wood having raised cork-like lines of near 177D.

*Resistance to disease.*—Average.

*Thorns (on main canes).*—Few and small in size.

*Thorns (on laterals).*—More than average, more and larger in size than those on the main stalk, up go 5/16 of an inch in length; positioned in very irregular manner; near R.H.S. 182B in color; sometimes straight and angled downward, sometimes curved slightly downward, both forms found on each stem.

*Prickles.*—None.

The miniature rose plant and its flowers as described herein will vary in color and perhaps in other slight detail due to climate, soil, and cultural conditions under which the variety may be grown; the present description being of the new variety as grown in two gallon pots outside in Essex County, Mass. in the month of September.

The following is claimed:

1. A new and distinct variety of miniature rose plant of hardy, upright, well branched yet open habit, substantially as illustrated and described, characterized primarily by its very strong, lilac-like fragrance; and by buds and flowers of medium to light mauve coloration, many borne on long stems suitable for use as cut flowers of for exhibition; resembling in size those of 'BENalav' except having fewer petals and being lighter in coloration; and further characterized by a plant of vigorous growth making it a good garden perennial or specimen plant, with small to medium sized, semi-glossy foliage, and being easy to propagate from cuttings.

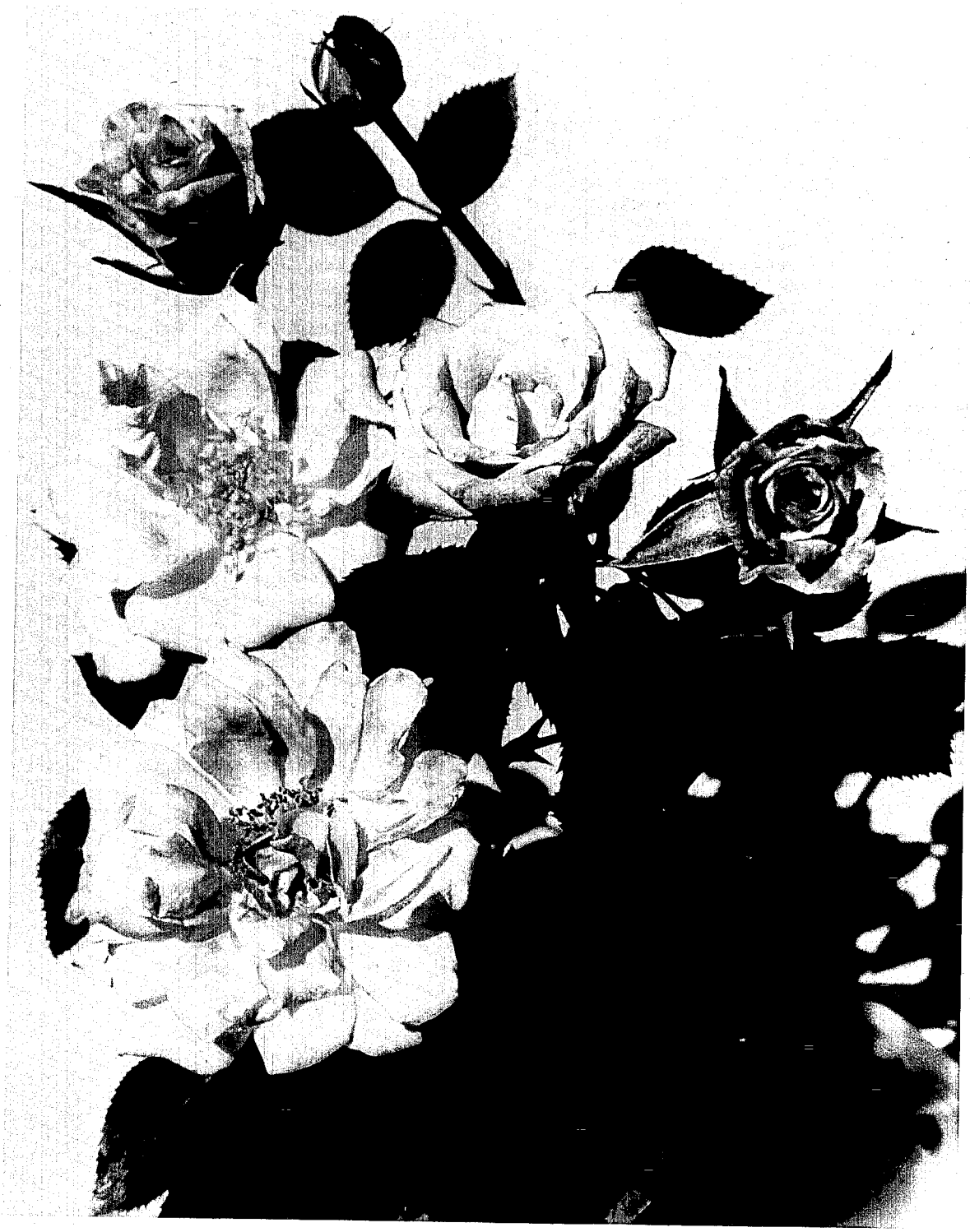

* * * * *